United States Patent [19]

Andersson et al.

[11] Patent Number: 4,641,644
[45] Date of Patent: Feb. 10, 1987

[54] AEROSOL INHALATION DEVICE

[75] Inventors: Jan A. R. Andersson, S Sandby; Nils F. E. Morén, Malmö ; Kjell I. L. Wetterlin, S Sandby, all of Sweden; Kaija A. Snellman Wasenius, Söderkulla; Risto Virtanen, Nurmijärvi, both of Finland

[73] Assignee: Aktiebolaget Draco, Sweden

[21] Appl. No.: 773,515

[22] Filed: Sep. 5, 1985

Related U.S. Application Data

[63] Continuation of Ser. No. 417,381, Sep. 13, 1982, abandoned.

[30] Foreign Application Priority Data

Sep. 15, 1981 [SE] Sweden ............................... 8105487

[51] Int. Cl.[4] ............................................. F11M 11/04
[52] U.S. Cl. ............................... 128/200.23; 239/451; 217/61; 220/252
[58] Field of Search ....................... 128/200.23, 200.14, 128/200.15, 200.16, 200.21, 203.15, 203.23, 203.24; 222/3, 635, 634, 631, 398, 519, 522–525; 239/788.5, 451, 455, 456, 499; 229/175 C; 217/61, 62; 220/252

[56] References Cited

U.S. PATENT DOCUMENTS

| 3,107,670 | 10/1963 | Silson et al. | 128/200.23 |
| 3,151,618 | 10/1964 | Wakeman | 128/200.23 |
| 3,184,115 | 5/1965 | Meshberg | 128/200.23 |
| 3,209,751 | 10/1965 | Wakeman | 128/200.23 |
| 3,456,644 | 7/1969 | Thiel | 128/200.23 |
| 3,506,004 | 4/1970 | Mann et al. | 128/200.23 |
| 4,130,116 | 12/1978 | Cavazza | 128/200.23 |
| 4,292,966 | 10/1981 | Mono et al. | 128/200.23 |
| 4,509,515 | 4/1985 | Altounyan et al. | 128/200.23 |

FOREIGN PATENT DOCUMENTS 1917913 10/1970 Fed. Rep. of Germany ....................... 128/200.23

Primary Examiner—Henry J. Recla
Assistant Examiner—Karin M. Reichle
Attorney, Agent, or Firm—Brumbaugh, Graves, Donohue & Raymond

[57] ABSTRACT

An aerosol inhalation device in pocket-size which has one dosage dispensing position and one storage position, and which comprises a two-part telescoping deceleration chamber (2, 3) with rectangular cross-section and a socket (1) for an exchangeable aerosol container. The socket is connected with the inner chamber part (2) so that it can be telescopically inserted therein to form a storage position. In dosage dispensing position the socket is extended from the deceleration chamber, pivoted at an angle relative to the longitudinal axis of the chamber and locked in the angle.

9 Claims, 9 Drawing Figures

Fig. 8
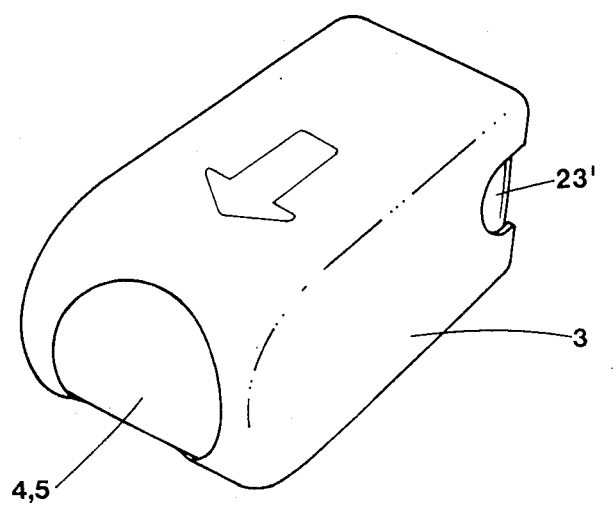
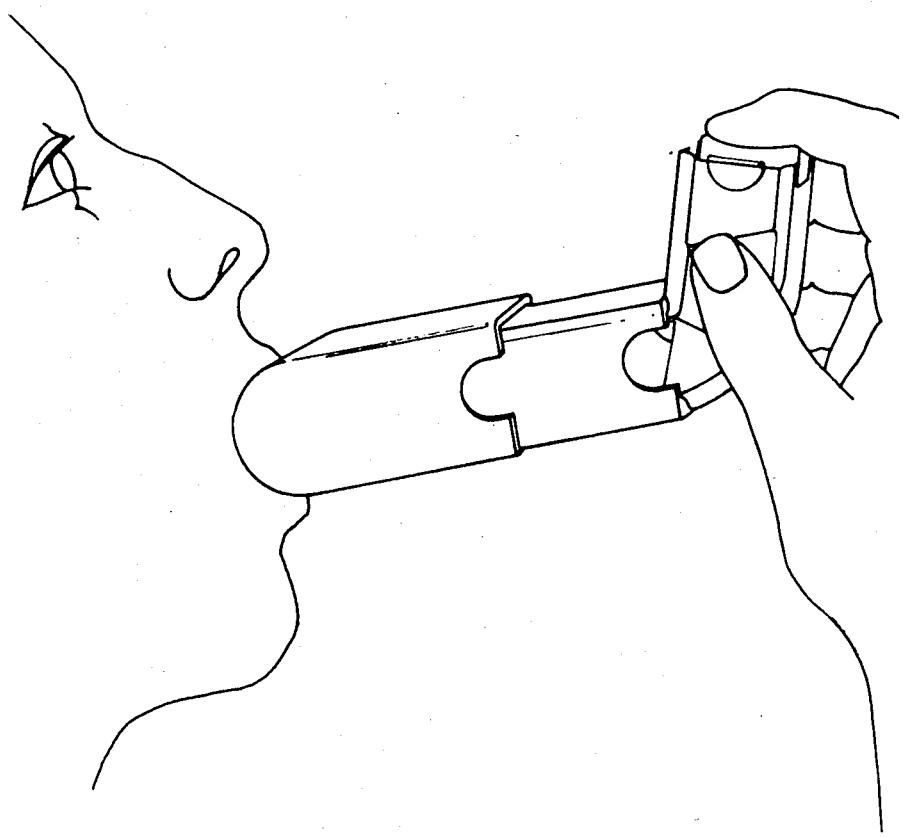
Fig. 9

AEROSOL INHALATION DEVICE

This application is a continuation of application Ser. No. 417,381, filed on Sept. 13, 1982, now abandoned.

TECHNICAL FIELD

The present invention relates to an aerosol inhalation device of a pocket size having one dosage dispensing position and one storage and transportation position. The device is provided with a long deceleration chamber but has in spite of this such a compact storage position that it can be carried conveniently in a pocket. The device can be made ready for dosage dispensing with a single hand grip in a rapid and simple manner.

BACKGROUND ART

Aerosol inhalation devices of a pocket size having one dosage dispensing position and a more compact storage position having previously been suggested. See for example U.S. Pat. Nos. 3,739,950, 3,809,294 and 3,994,421. The device according to the present invention differs from the devices disclosed in said patents inter alia because it is provided with a considerably longer and more efficient deceleration chamber and is yet so compact that it can be carried in a pocket. Furthermore, the device according to the invention comprises only three different parts that can be produced by injection molding and then be assembled with a few simple hand grips. The device can also be switched over from storage position to dosage dispensing position in a simple and rapid way.

European Patent Application No. 80 85 0006.0 (Publication No. 0 015 247) discloses an aerosol inhalation device which has a two part telescopic deceleration chamber. The device according to the present invention constitutes an improvement of the device disclosed in said European Patent Application and is advantageous inter alia because it has a more compact storage position compared with the dosage dispensing position. This advantage has, according to the invention, unexpectedly been attained by simple structural means.

SUMMARY OF THE INVENTION

The present invention relates to an aerosol inhalation device having one storage position and one dosage dispensing position for use at inhalation of uniform doses of a finely divided drug in the form of an aerosol, comprising a socket for an exchangeable aerosol container and an elongated deceleration chamber connected to the socket, said chamber having a mouthpiece in its opposite end and intended to be connected to the mouth of a patient; the chamber comprises two chamber parts, each preferably having a substantially rectangular cross section, of which an outer chamber part comprises the mouthpiece and is telescopically displaceable over an inner chamber part which is provided with a flexible tongue at the end being adjacent the mouthpiece, which tongue on telescoping the device together will close the mouthpiece, which aerosol inhalation device is configured so that the socket for the aerosol container:

(a) has preferably a substantially rectangular cross section and can be telescopically inserted into said inner chamber part to a storage position, (b) is tapered by a sectional arch in the end being adjacent the chamber and is provided with grooves alongside its four longitudinal edges, which grooves are each terminated with a stop lug which in the dosage dispensing position catch with stop lugs in the inner chamber part so that the socket can be extracted from said chamber part and be pivoted in a fixed angle relative the longitudinal axis of the chamber part to assume the dosage dispensing position and (c) is provided with means for locking the socket in said fixed angle.

BRIEF DESCRIPTION OF THE DRAWINGS

The invention is explained in detail in the following, inter alia with reference to the specific embodiment shown in the annexed drawings wherein:

FIG. 8 is a perspective view of the inhalation device in its storage position; and FIG. 9 is a perspective view that illustrates how the inhalation device is to be held during dosage dispensing and inhalation.

DETAILED DESCRIPTION OF THE PREFERRED EMBODIMENT

The specifically illustrated inhalation device consists of two main parts, viz. a socket 1 for an exchangeable aerosol container and a long two part deceleration chamber 2, 3 being connected to the socket. The deceleration chamber has an outlet or mouthpiece 4 in the opposite end intended to be inserted in the mouth of a patient. The purpose and design of the deceleration chamber is essentially identical with the deceleration chamber specifically disclosed in European Patent Application No. 80 85 0006.0.

Figure 5:
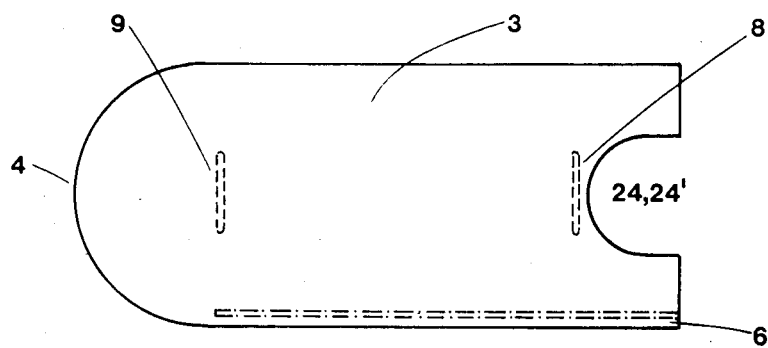
FIGS. 5-7 are plan side views of each one of the three parts of the inhalation device.
Figure 6:
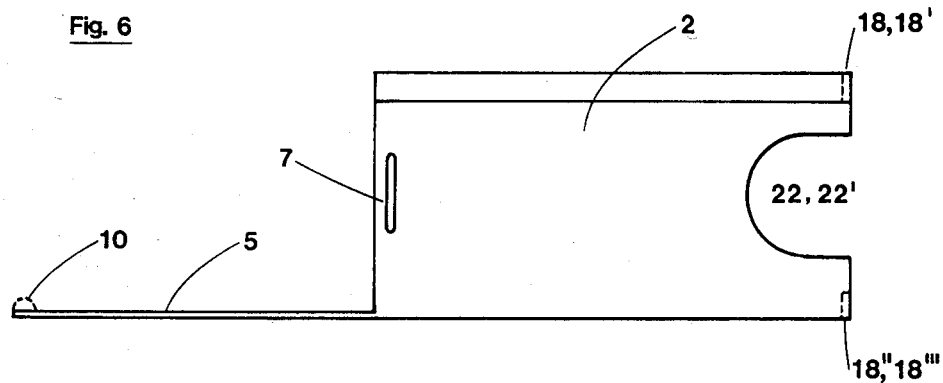
Figure 7:
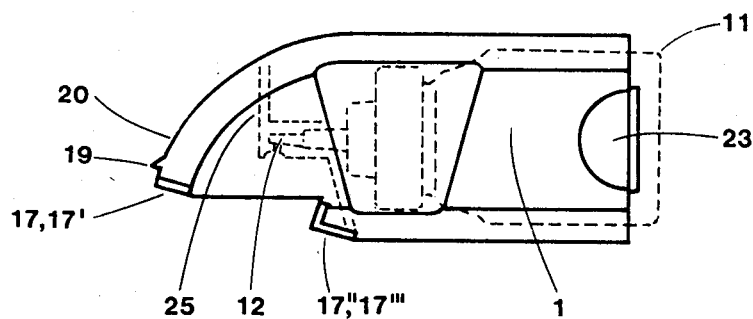

The deceleration chamber thus comprises two chamber parts 2, 3 each preferably having a substantially rectangular cross section. The outer chamber part 3, which comprises the mouthpiece 4, is telescoping over an inner chamber part 2. The said inner chamber part is provided with a flexible tongue 5 in the end turned against the mouthpiece 4. The tongue is slidably arranged along the inner side of one of the walls of the outer chamber part, so that the tongue will be displaced to close the mouthpiece when the two chamber parts are pushed together. The flexible tongue is integral with the inner chamber part, end the tongue is guided along and close to an inner wall of the outer chamber part by guiding means or guiding rails 6 (illustrated with a dot-dashed line in FIG. 5) which are arranged inside the outer chamber part. A projecting locking edge 7 on the outside of the inner chamber part fits with two recessions 8, 9 on the inside of the outer chamber part, which recessions are situated at some distance from each other. The locking edge 7 and the recessions 8, 9 can advantageously be doubled, so that there will be locking edges and recessions on two opposite sides of the chambers. The purpose of the locking edges and recessions is to limit the telescoping of the chamber parts to suitable end positions for storage and dosage dispensing, respectively, and to lock the chamber parts in these end positions, and also to provide a safeguard against undesired disassembly of the parts. In order to obtain further safety against disassembly, the tongue may be provided with stop lugs 10 (illustrated by a dashed line in FIG. 6) on each side of the tongue and at the outermost end thereof, which stop lugs only with difficulty can be pulled through the guiding rails 6.

The other main part of the inhalation device comprises a socket 1 for an exchangeable aerosol container 11. This socket is designed and connected with the inner chamber part 2 of the deceleration chamber in such a way that the socket, together with the aerosol container 11 therein, can be telescopically inserted in the inner chamber part 2 to obtain a storage position. In connection with dosage dispensing, the socket 1 is pulled out of the inner chamber part, whereby at the same time the inner chamber part is pulled out of the outer chamber part 3 so that the tongue 5 is withdrawn and opens up the mouthpiece 4. The socket is then turned a fixed angle (preferably between 30°–90°) in relation to the longitudinal axis of the chamber and is then locked at said angle.

The inhalation device is intended to be held by a patient at a dosage dispensing in the manner illustrated in FIG. 9. Because the socket is turned upwards at an angle against the deceleration chamber the device as a whole can be held comfortably and safely, whereby furthermore an exchangeable standard type aerosol container can be used. The term "standard type aerosol container" relates to a pressurized container containing the active substance dissolved or suspended in a propellant usually consisting of a chloro-fluoro-substituted hydrocarbon. The container has a displaceable discharge outlet being connected to a dosage dispensing appliance in the form of a spring-loaded valve system. The dosage dispensing appliance is filled with a mixture of propellant and drug when the container is held upside-down, and a dose of the mixture can be made to discharge from the container when the discharge outlet is pushed into the container. The socket 1 is provided with an interior, centrally mounted duct 12 and the discharge outlet of the container is inserted in this duct with finger friction fit. The term "finger friction fit" is used to denote a frictional relationship which will hold the pieces together under normal handling conditions, but may be readily disengaged or engaged by finger pressure only. The interior duct 12 in the socket is tapering and bent, and leads straight out into the longitudinal direction of the deceleration chamber when the socket is extended and locked in the dosage dispensing position.

Dosage dispensing takes place when the aerosol container is pushed downwards in the socket, whereby the discharge outlet of the container is pushed into the container so that a dose of drug is discharged into the deceleration chamber.

The socket is provided with interior guide rails 13, 13', 13'', 13''' which center the aerosol container when it is inserted in the socket, and thus indirectly center the discharge outlet of the container so that it is guided into the discharge outlet of the container so that it is guided into the discharge duct in the socket. Furthermore, the socket is provided with notches 14, 14' at two opposite sides thereof to facilitate the withdrawal of the container when substituting the container with a new one. The design of the socket should be such that no part of the aerosol container extends from the outermost end of the device in the storage position. Otherwise there would be a risk for discharge of an aerosol dose in response to an unintentional pressure or touch of the container when it is carried in a pocket.

Two opposite outer sides of the socket are provided with finger holds in the form of recessions 15, 15'. These are intended for holding the inhalation device in a stable and comfortable manner in the dosage dispensing position, as illustrated in FIG. 9.

The socket is, as previously mentioned, both extendable and hinged in relation to the inner chamber part of the deceleration chamber. This property of the socket has in the embodiment particularly shown, been attained by housing the socket rounded off by a circular sectional arch in the end being adjacent the chamber, as well as by the socket being provided with grooves 16, 16', 16'', 16''' alongside all its four longitudinal edges. These grooves are each terminated with a stop lug 17, 17', 17'', 17''' in the ends which are adjacent the chamber. In the dosage dispensing position, these stop lugs catch with stop lugs 18, 18', 18'', 18''' mounted in the outer end of the inner chamber part and prevent further pivoting or extraction of the socket from the inner chamber part. The socket is automatically locked in the pivoted position with the aid of a further stop lug 19 which is mounted close to the end of the arched section of the socket. This stop lug 19 is mounted on a short flexible tongue 20 which has been obtained by two elongated notches 21, 21' cut on each side of the stop lug 19. The stop lug may then be released, in a simple way, from the edge of the inner chamber part by finger pressure on the tongue when the socket, at the return to the storage position, is to be pivoted back in a straight line with the longitudinal axis of the chamber parts and pushed into the inner chamber part.

In order to make it possible to push the socket completely into the inner chamber part to the storage position, as illustrated in FIG. 8, but yet make it possible to easily extract the socket from the chamber part when preparing for dosage dispensing, a U-shaped notch 22, 22' is arranged in each of the two side-walls of the inner chamber part, and these notches correspond to U-shaped stop lugs 23, 23' mounted in the outer end of the socket. In storage position these stop lugs are inserted to catch with the notches being open backwards. Because corresponding U-shaped notches 24, 24' are arranged also in the outer chamber part it is easy to extract the socket from the chambers by gripping the both stop lugs 23, 23' with the thumb and forefinger of one hand and then gripping around the outer chamber part with the other hand. When taking the hands apart the socket will be extracted from the inner chamber part and can then be pivoted to the intended angle and locked. At the same time, the inner chamber part is extracted from the outer chamber part and is locked in the extended position whereupon dosage dispensing can commence. The whole switch over of the inhalation device from the storage position to start of inhalation can be made in just a few seconds.

Figure 1:
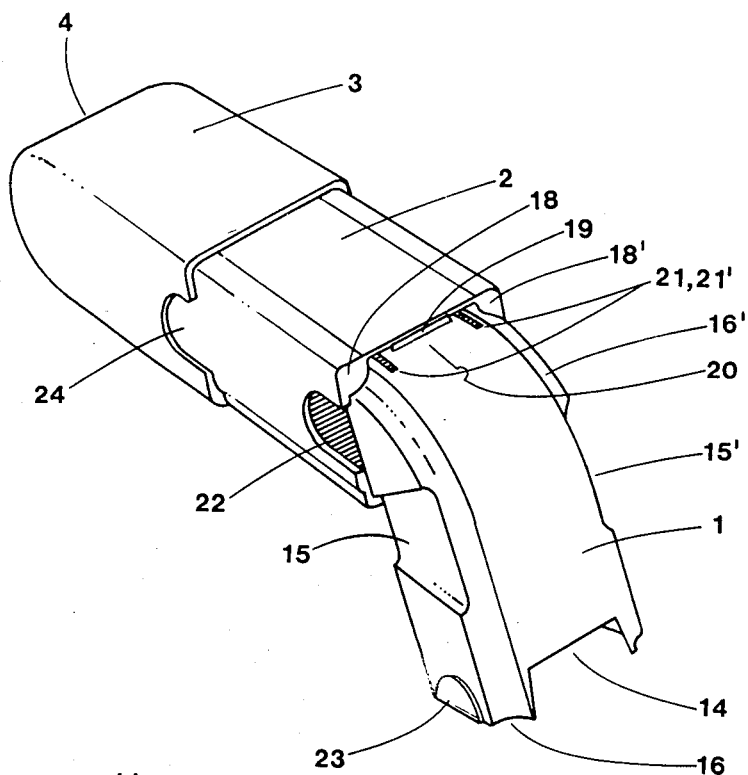
FIG. 1 is a perspective view of an aerosol inhalation device according to the invention in a dosage dispensing position, shown from below and without an aerosol container.
Figure 2:
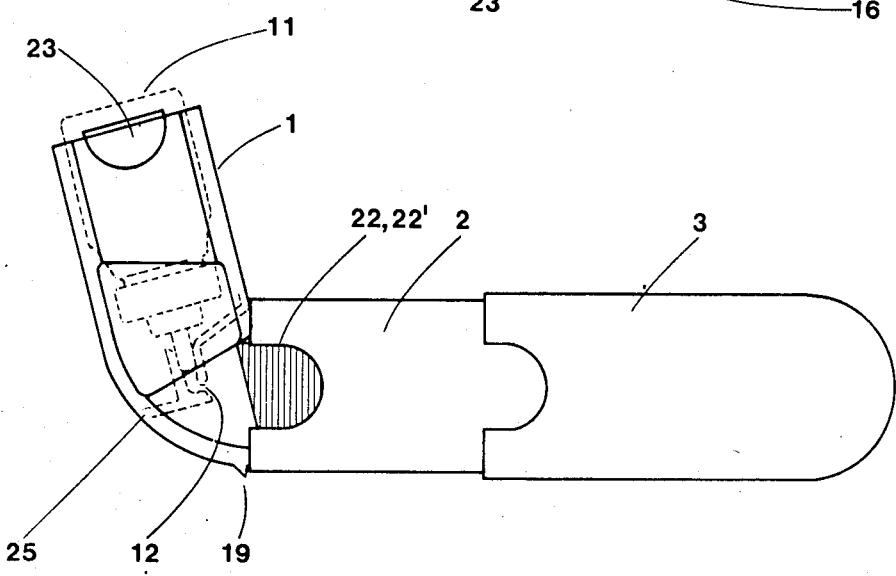
FIG. 2 is a plan side view of the inhalation device in its dosage dispensing position and with the aerosol container shown with broken lines.
Figure 3:
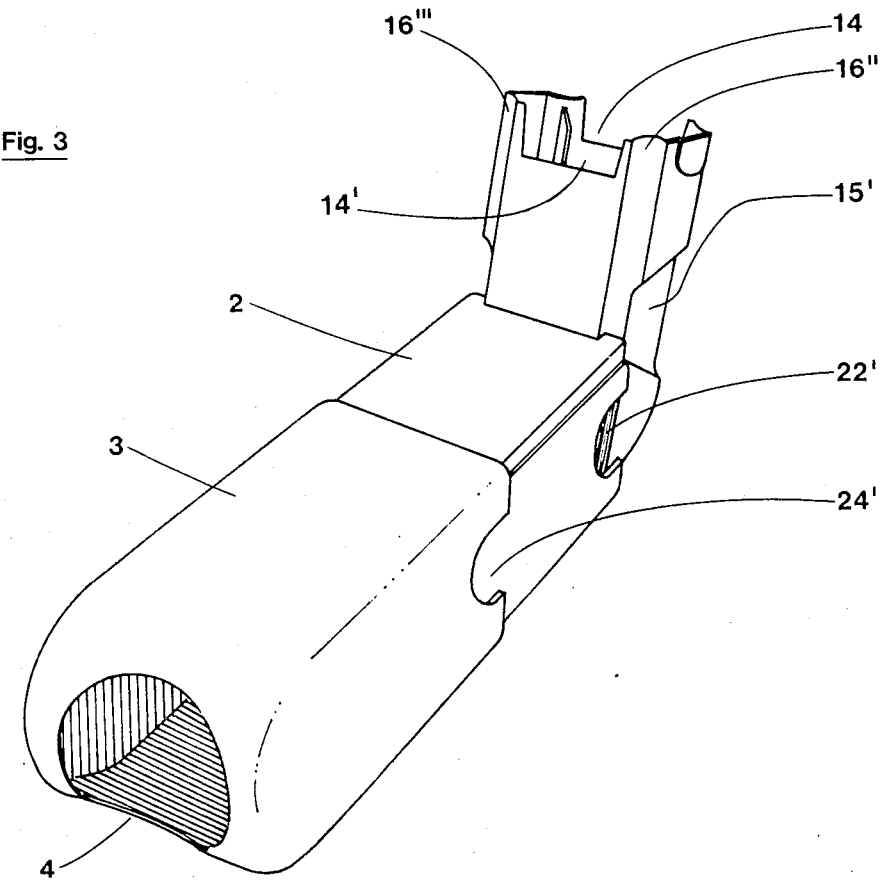
FIG. 3 is a further perspective view of the inhalation device in its dosage dispensing position but shown without aerosol container.
Figure 4:
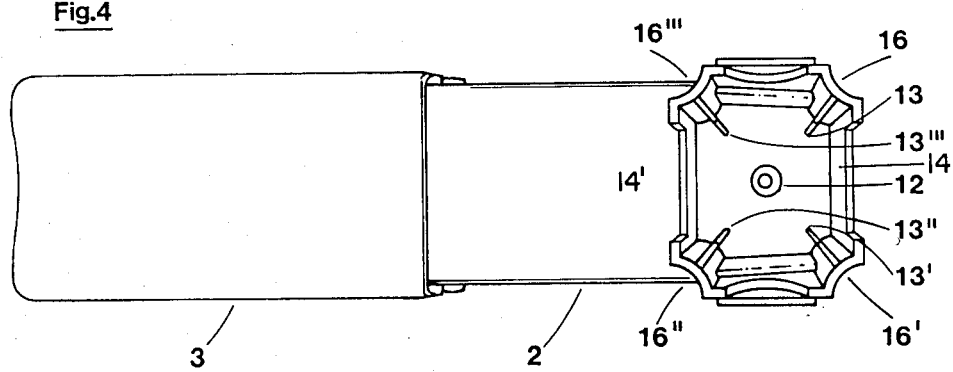
FIG. 4 is a perspective view of the inhalation device in its dosage dispensing position, shown from the longitudinal direction of the socket for the aerosol container but without said container.

As is shown in e.g. FIG. 1, both U-shaped notches 22, 22' form free openings towards the surrounding air when the device is in the dosage dispensing position. These free openings comprise the sole air inlets for diluent air at inhalation, and these air inlets are thus open only in the dosage dispensing position. Because the socket furthermore has a partition wall 25 which is only penetrated by a very narrow duct, and because the mouthpiece 4 is closed by the tongue in the storage position, the inner space of the inhalation device is, when in the storage position, automatically protected against pollution from dust etc.

The three parts of the aerosol inhalation device are most simply produced by conventional injection molding of a plastics material such as LD-polyethene, HD-polyethene, or polypropene. The inner chamber part may suitably be provided with a couple of small external and internal longitudinal ribs having a height of between 0.05–0.5 mm, in order to provide suitably strong friction against the socket and the outer chamber part. By having such small ribs, the natural resilience of plastics is utilized to give a stable connection between the different parts without expensive requirements as to accuracy during production, and at the same time, the parts can easily be displaced relative to each other by finger pressure only.

Due to the natural resiliency of plastics, the three parts of the inhalation device can easily be assembled. The socket is thereby pushed into the inner chamber part from that side of the chamber having the tongue attached, whereupon the tongue is inserted in the guiding rails in the outer chamber part. Finally, the inner chamber part with the socket is pushed into the outer chamber in such a way that the tongue is first inserted in the guiding rails whereupon the locking edge 7 catches in the recession 9 in the outer chamber part.

The length of the deceleration chamber of the inhalation device is suitably 10–20 cm in the dosage dispensing position. In the embodiment shown in the drawings, the length of the deceleration chamber is 13 cm, the width is 3.8 cm and the height is 3.4 cm. The total length of this embodiment in the dosage dispensing position is 17 cm, but in the storage position the total length is only 8 cm.

What is claimed is:

1. An aerosol inhalation device for administering a finely divided drug by inhalation, comprising
    a socket having a substantially rectangular cross-section comprising two side walls, a top wall and a bottom wall, said walls defining a duct having a first open end adapted to receive an aerosol container of the drug and a second open end through which aerosol discharged from the container can exit and adapted to receive a discharge valve of the aerosol container and direct the aerosol discharged thereby through said second open end;
    an elongated deceleration chamber having a substantially rectangular cross-section and defining a duct, said chamber comprising an inner chamber portion and an outer chamber portion, each chamber portion including two side walls, a top wall, a bottom wall and opposite first and second open ends, said outer chamber portion having its first open end telescopically displaceable over the second open end of said inner chamber portion between an extended position for dispensing aerosol doses, wherein the first open end of said outer chamber portion overlies the second open end of said inner chamber portion, and a collapsed position for storage of said device, wherein the first open end of said outer chamber portion overlies the first open end of said inner chamber portion, said deceleration chamber having a mouth piece at said second end of said outer chamber portion; and
    means for operatively connecting the second open end of said socket and the first end of said inner chamber portion so that said chamber receives the aerosol discharged from the aerosol container, said operative connection means comprising;
    a sectional arch defined by the portion of said socket adjacent said second open end, said arch formed by the side walls and the top wall adjacent said second open end extending beyond the plane perpendicular to the end of the bottom wall adjacent said second open end and curving toward the plane containing the bottom wall, and wherein the second open end of said socket is defined between the opening formed by the end of the top wall, the end of the bottom wall and the ends of the two side walls, said sectional arch being inserted into the first open end of said inner chamber portion with said top, side and bottom walls of said socket adjacent the respective ones of the inner chamber portion, said arch pivots about a pivot axis located substantially within the plane of the bottom wall of the socket and substantially within the plane of the bottom wall of the inner chamber portion to guide said socket through an angle to said deceleration chamber as said socket is moved to an extended position, wherein said socket extends out of said inner chamber portion, from a collapsed position, wherein said socket is contained within said inner chamber portion and back again; and
    locking means on said socket and on said inner chamber portion for maintaining said socket and inner chamber portion at said angle when said socket is in its extended position.

2. A device according to claim 1, wherein said locking means includes:
    a flexible tongue in the curved top wall defining the sectional arch, said tongue being defined by two spaced slots through the curved top wall which extend axially therealong to the end thereof adjacent said second open end, and a stop lug located on the exterior surface of the tongue adjacent the end of the top wall adjacent said second open end, said stop lug being capable of catching the end of the top wall of the inner chamber portion in the extended position of said socket to prevent the socket from being moved back into said chamber, and
    lug means on said socket and mating lug means on said inner chamber portion, said lug means and mating lug means being adapted to engage each other when the socket is in the extended position to thereby prevent the socket from moving beyond said angle, whereby said locking means maintains said socket and said inner chamber portion restrained from all relative rotational and translational movement when said socket is in its extended position.

3. A device according to claim 2, wherein said lug means includes a plurality of stop lugs located at the second open end of said socket and wherein said mating lug means includes a plurality of corresponding stop lugs located at the first open end of said inner chamber portion.

4. A device according to claim 1, wherein said inner chamber portion includes flexible tongue means, located at the second open end thereof, for closing said mouthpiece in the outer chamber portions collapsed position.

5. A device according to claim 1, wherein the inner chamber portion has mating guide means comprising guiding lugs at the first end of the inner chamber portion and wherein the socket has guide means comprising longitudinal grooves along the longitudinal exterior edges of said socket to receive said guiding lugs of said mating guide means.

6. A device according to claim 1, wherein the socket has a recess in the exterior surface of each side wall, said recesses defining finger grips intended for holding the device in the extended position of the socket.

7. A device according to claim 1, wherein said socket includes guiding rails extending inwardly into said socket duct adapted to guide and hold the aerosol container in said socket duct, said guiding rails being capable of guiding the discharge valve of the aerosol container into engagement with the means adapted to receive the discharge valve.

8. A device according to claim 1, wherein the socket has a notch in each of said top and bottom walls at the first open end of said socket.

9. An aerosol inhalation device for administering a finely divided drug by inhalation, comprising:
 a socket having a substantially rectangular cross-section comprising two side walls, a top wall and a bottom wall, said walls defining a duct having a first open end adapted to receive an aerosol container of the drug and a second open end through which aerosol discharged from the container can exit and means adapted to receive a discharge valve of the aerosol container and direct the aerosol discharged thereby through said second open end;
 an elongated deceleration chamber having a substantially rectangular cross-section and defining a duct, said chamber comprising an inner chamber portion and an outer chamber portion, each chamber portion including two side walls, a top wall, a bottom wall and opposite first and second open ends, said outer chamber portion having its first open end telescopically displaceable over the second open end of said inner chamber portion between an extended position for dispensing aerosol doses wherein the first open end of said outer chamber portion overlies the second open end of said inner chamber portion, and a collapsed position for storage of said device, wherein the first open end of said outer chamber portion overlies the first open end of said inner chamber portion, said deceleration chamber having a mouthpiece at said second end of said outer chamber portion; and
 means for operatively connecting the second open end of said socket and the first end of said inner chamber portion so that said chamber receives the aerosol discharged from the aerosol container, said operative connection means comprising:
 a sectional arch defined by the portion of said socket adjacent said second open end, said arch formed by the side walls and the top wall adjacent said second open end extending beyond the plane perpendicular to the end of the bottom wall adjacent said second open end and curving toward the plane containing the bottom wall, and wherein the second open end of said socket is defined between the opening formed by the end of the top wall, the end of bottom wall and the edges of the two side walls, said sectional arch being inserted into the first end of said inner chamber portion with said top, side and bottom walls of said socket adjacent the respective ones of the inner chamber portion, said arch guides said socket through an angle to said deceleration chamber as said socket is moved to an extended position, wherein said socket extends out of said inner chamber portion, from a collapsed position, wherein said socket is contained substantially completely within said inner chamber portion and back again;
 said socket being provided with guide means along said arch and along the remaining length of said socket, and said inner chamber portion being provided with mating guide means at the first end of said inner chamber portion, said guide means and mating guide means being adapted to cooperate with each other when the second end of the socket is inserted into the first open end of said inner chamber portion to guide said socket through said angle to said chamber as it is moved from its collapsed position to its extended position at said angle relative to said chamber; and
 locking means on said socket and on said inner chamber portion for mating with and engaging with each other to maintain said socket and inner chamber portion at said angle when said socket is in its extended position, said socket being moveable into said inner chamber portion guided by said guide means and mating guide means;
wherein said socket has outwardly projecting stop lugs on the exterior surface of said side walls and located at the first open end and wherein notches are provided in the inner chamber portion side walls located at the first open end thereof, said notches being air inlets for diluent air in the extended position of said socket and being positioned relative to said outwardly projecting stop lugs of said socket to catch the outwardly projecting stop lugs and prevent insertion of said socket into said inner chamber portion beyond its collapsed position.

* * * * *